United States Patent [19]

Dabrowski et al.

[11] Patent Number: 4,849,130
[45] Date of Patent: Jul. 18, 1989

[54] LIQUID CRYSTALLINE ETHANE DERIVATIVES, THEIR PREPARATION AND THE LIQUID CRYSTAL COMPOSITIONS CONTAINING SAME

[75] Inventors: Roman Dabrowski; Jerzy Dziaduszek; Tomasz Szczucinnski, all of Warsaw; Witold Drzewiński, Blizne-Laszcz; Zofia Stolarz, Warsaw; Józef Żmija, Warsaw; Janusz Parka, Warsaw; Bożena Sosnowska, Warsaw, all of Poland

[73] Assignees: Wojskowa Akademia Techniczna; Zaklady Kineskopowe "Unitra-Polkolor" Zaklady Kineskopow Kolorowych, both of Poland

[21] Appl. No.: 176,253

[22] Filed: Mar. 31, 1988

Related U.S. Application Data

[63] Continuation-in-part of Ser. No. 942,391, Dec. 16, 1988.

[30] Foreign Application Priority Data

Dec. 16, 1985 [PL] Poland ................................ 256832

[51] Int. Cl.$^4$ ...................... C09K 19/34; C09K 19/30; C09K 19/14; C07C 161/04; C07D 319/06; C07D 239/26

[52] U.S. Cl. ............................ 252/299.61; 252/299.6; 252/299.62; 252/299.63; 252/299.66; 350/350 R; 350/350 S; 544/242; 544/294; 544/296; 544/298; 544/316; 544/335; 549/370; 549/372; 549/373; 558/17; 558/18; 558/19

[58] Field of Search ............ 252/299.6, 299.61, 299.62, 252/299.63, 299.66; 350/350 R, 350 S; 558/17, 18, 19; 549/372, 373, 370; 544/242, 294, 296, 298, 316, 335

[56] References Cited

U.S. PATENT DOCUMENTS

| | | | |
|---|---|---|---|
| 4,035,056 | 7/1977 | Coates et al. | 252/299.66 |
| 4,261,651 | 4/1981 | Grat et al. | 252/299.63 |
| 4,400,293 | 8/1983 | Romer et al. | 252/299.63 |
| 4,528,116 | 7/1985 | Dabrowski et al. | 252/299.63 |
| 4,621,901 | 11/1986 | Petrzilfa et al. | 252/299.6 |
| 4,630,896 | 12/1986 | Petrzilfa et al. | 252/299.63 |
| 4,652,089 | 3/1987 | Oesterhelt et al. | 252/299.63 |
| 4,659,502 | 4/1987 | Fearon et al. | 252/299.62 |
| 4,767,924 | 6/1987 | Dabrowski et al. | 252/299.61 |
| 4,770,503 | 9/1988 | Buchecker et al. | 252/275.63 |

FOREIGN PATENT DOCUMENTS

| | | | |
|---|---|---|---|
| 169327 | 1/1986 | European Pat. Off. | 252/299.63 |
| 3545345 | 7/1987 | Fed. Rep. of Germany | 252/299.61 |
| 60-136555 | 7/1985 | Japan | 252/299.61 |
| 60-146868 | 8/1985 | Japan | 252/299.63 |
| 60-204781 | 10/1985 | Japan | 252/299.61 |
| 60-222458 | 11/1985 | Japan | 252/299.63 |
| 61-43172 | 3/1986 | Japan | 252/299.61 |
| 61-158957 | 7/1986 | Japan | 252/299.63 |
| 61-189263 | 8/1986 | Japan | 252/299.63 |
| 8603769 | 7/1986 | World Int. Prop. O. | 252/299.61 |

OTHER PUBLICATIONS

Dabrowski, R., et al., Mol. Cryst. Liq. Cryst., vol. 102 (letters), pp. 155-160 (1984).
Dabrowski, R., et al., Mol. Cryst. Liq. Cryst., vol. 87, pp. 109-135 (1982).
Demus, D., et al., Flussile Kristalle in Tabellen II, VEB Deutscher Verlag for Grundstoffindustrie, Leipzig, p. 130 (1984).
Dabrowski, R., et al., Mol. Cryst. Liq. Cryst., vol. 107, pp. 411-443 (1984).
Dabrowski, R., et al., J. Physique (Paris), vol. 45, pp. 1213-1222 (1984).
Baran, J. W., et al., Mol. Cryst. Liq. Cryst., vol. 123, pp. 237-245 (1985).
Dabrowski, R., et al., Mol. Cryst. Liq. Cryst., vol. 124, pp. 241-257 (1985).

Primary Examiner—Teddy S. Gron

[57] ABSTRACT

Liquid crystalline ethane derivatives by the described method in order to form liquid crystalline compositions with known liquid crystalline compounds have a general formula I:

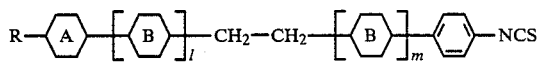

I wherein, if ring A idicates a 1,4-substituted benzene ring, then ring B indicates 1.4-substituted benzene ring or 1.4-trans-substituted cyclohexane ring or 1.4-substituted bicyclo[2,2,2]octane ring or 2.5-substituted pyrimidine ring or 2.5-substituted 1.3- dioxane ring, or if ring B indicates a 1.4-substituted benzene ring, then A indicates 1.4-trans-substituted cyclohexane ring or 1.4-substituted bicylo[2,2,2]octane ring or 2.5-substituted pyrimidine ring or 2.5-substituted 1.3-dioxane ring, and R indicates a normal alkyl chain $C_nH_{2n+1}$ or a non-branched alkoxy group $C_nH_{2n+1}O$ or an alkylcarboxylic group $C_nH_{2n+1}COO$ or an alkyl carbonato group $C_nH_{2n+1}OCOO$ or a branched alkyl chain $CH_3$—$CH_2$—$CH(CH_3)$—$(CH_2)_k$— or a branched alkoxy group $CH_3$—$CH_2$—$CH(CH_3)$—$(CH_2)_k$—O, where n is an integer number and assumes values from 1 to 12, k is an integer number and assumes values from 1 to 3 and l and m assume values 1 or 0 fulfilling the condition that 1+m>0, and if ring A denotes 1.4-disubstituted bicyclo[2,2,2]octane ring also 1+m=0. Liquid crystalline compositions containing the compound of formula I are characterized by low viscosity and are applied in displays.

12 Claims, No Drawings

LIQUID CRYSTALLINE ETHANE DERIVATIVES, THEIR PREPARATION AND THE LIQUID CRYSTAL COMPOSITIONS CONTAINING SAME

This Application is a continuation-in-part of our United States Patent Application, Ser. No. 942,391 filed Dec. 16, 1988.

FIELD OF THE INVENTION

The present invention relates to liquid crystalline compounds and mixtures.

DESCRIPTION OF THE PRIOR ART

The liquid crystalline materials known so far are applied in various displays as example digital watches, calculators and so on. The scope of application of displays using liquid crystals is very rapidly increasing. At the moment they are also applied in various types of control instruments, in terminals of computers, in electronic games, in flat television screens and so on. They are also applied in instruments working in changing external conditions, as parking meters, pump meters at gasoline stations, car dashboards, various types of portable instruments.

The development of liquid crystalline display applications requires liquid crystalline materials of improved properties ensuring reliable work of the display not only in closed rooms, where the working conditions change very little, and also in open-door conditions, where the temperature, humidity and ultraviolet radiation intensity greatly varies.

Liquid crystalline displays are usually constructed in such a way, that the layer of the liquid crystal of 7 to 11 $\mu$m thick is placed between two transparent, electrically insulated substrates (usually these are glass plates). An electrode structure is mounted on them enabling voltage application to the layer of the liquid crystal. The electric voltage applied to the chosen element of the electrodes causes a change in the arrangement of the liquid crystal molecules in layer, what in turn causes a visible optical effect in this region and is used in order to present information in the form of series of letters, figures or a graphs.

There is a large number of different effects which can result from reorientation of liquid crystal molecules by electric field. This is dependent on the type of the used liquid crystalline material as well as on the initial molecular arrangement of the liquid crystalline layer. The most frequently used effect in displays is the twisted nematic effect. In the twisted nematic effect, the liquid crystalline material is in its initial state arranged (electric field switched off) in parallel to the surface of the substrate through the action of the surface forces of the substrates in such a way, that when passing from the surface of one glass substrates to the surface of the second glass substrates, the long axis of the molecules are most frequently twisted by an angle of 90°. Such an arrangement is optically active, i.e. it rotates the plane of polarization of light. After applying a voltage larger than the threshold voltage, reorientating the molecules, the twist structures is destroyed and the liquid crystalline layer looses its optical activity. It a liquid crystalline layer arranged according to the presented rule is placed between the polarizers, it behaves as an optical valve, and is switched over by the field from the bright state to the dark one, depending on whether the two polarizers are connected in parallel with each other or perpendicularly.

If a dichroic dye, or a mixture of dyes, is placed in a liquid crystalline layer then switching over from a bright state to dark state or from a bright state to a colured state or from a coloured state to a bright state, can be attained using one polarizer only. If we apply the cholesteric-nematic phase change effect and dichroic dyes, we do not require polarizers and the twist structure of the liquid crystalline layer in order to display. Liquid crystalline materials of positive dielectric anisotropy are required for the twisted nematic effect and the cholestericnematic phase change effect.

Static and dynamic electrooptical characteristics of liquid crystalline displays are related to dielectric anisotropy, optical anisotropy, elastic constants and viscosity of the liquid crystalline material. The basic problem, arising when applying nematic liquid crystalline materials in displays, is obtaining stable substances of low viscosity. Low viscosity of liquid crystalline material enables construction of fast operating displays. Especially advantageous are such materials which have a low dependance of viscosity from temperature, as liquid crystalline displays containing them will have reaction times hardly dependent on temperature.

No single liquid crystalline substance has characteristics fulfilling requirements demanded from liquid crystalline materials. According to the present art, a material of better performance in displays can be formed by mixing a few or a dozen so different compounds. Non-liquid crystalline compounds and also compounds showing optical activity and dyes, can also be introduced to the material composed liquid crystalline compounds whose individual components are with nematic or sometimes smectic properties. A mixture composed of appropriately chosen compounds satisfies the requirements of the liquid crystalline material for definite application more sufficiently. Such a mixture of course, has to be resistant to light, humidity, heat, oxygen and usually such compositions are prefered which have a low threshold voltage and a low supply voltage required for steering the display and which are characterized by a wide mesophase range. In order to obtain a liquid crystalline mixture of a wide mesophase range components are chosen in such a way as to form a basic composition of mesogenes of lowest melting point, to which 5-30% of tri- and tetra ring compounds are introduced. The basic mixture is formed from small double ring molecules most frequently being derivatives of azoxybenzene, biphenyl, phenylcyclohexane, phenylpyrimidine, phenyldioxane. Examples of such compounds are show in patents: Pol. Pat. No. 107,551, GB Pat. No. 1,433,130, West Germany Pat. No. 2,636,684, West Germany Pat. No. 2,547,737, U.S. Pat. No. 4,322,354, GDR Pat. No. 139,852. The most frequently used compounds broadening the mesophase range are cyano derivatives of terphenyl, cyclohexylbiphenyl, diphenylpyrimidine or esters of cyclohexylbenzoic or biphenyric acids, the examples are given in patents: GB Pat. No. 1,433,130, West Germany Pat. Nos, 2,545,121, 2,701,591, 2,708,276, 2,899,533. The above mentioned tri- or tetra ring liquid crystalline compounds applied as components of the liquid crystalline mixture increase its clearing temperature but at same time their viscosity unfavaroubly increases. And so most favourable would be such compounds, which would broaden the mesophase range of the mixture with very slight changes in their viscosity.

Recently, multiring non-polar hydrocarbons with dimethylene flexible bridges between the rings (M. Schadt, Mol.Cryst.Liq.Cryst., 34, 138, (1983)) have been proposed in order to fulfil the above requirements. These compounds are characterized by small negative or positive dielectric anisotropy and therefore their presence in the composition decreases its resultant positive anisotropy. This leads to increase of threshold voltages of such mixtures. And so it would be more advantageous to apply compounds of similar characteristics concerning viscosity but having a large dielectric anisotropy.

A new class of liquid crystalline compounds 4-(trans-4-n-alkylcyclohexyl)benzenoisothiocyanates, which are characterized by very small viscosity, and low melting point, and allow to form basic compositions of low viscosity about 10 cP, have been described in the U.S.A. Pat. No. 4,528,116. However these compounds have a moderate anisotropy and so the above mentioned hydrocarbons are less applicable for broadening the mesophase range.

More advantageous would be compounds of larger positive dielectric anisotropy and having simultaneously different values of optical anisotropy. Polar tri-ring compounds having a terminal CN group are slightly soluble and less stable in 4-(trans-4-n-alkylcyclohexyl)benzeneisothiocyanates.

SUMMARY OF THE INVENTION The present invention is concerned with novel ethane derivatives having a polar isothiocyanato group in the terminal position of molecule and with their use as components of liquid crystal mixtures for electrooptical purposes. The invention is also related to their preparation. These are compounds of general formula I:

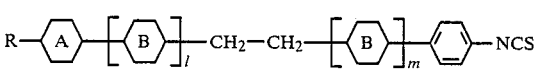
I wherein
rings A and B are identical or different and when ring A indicates 1,4-substituted benzene ring

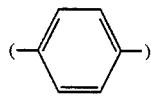

then ring B indicates 1,4-substituted benzene ring or 1,4-trans-substituted cyclohexane ring

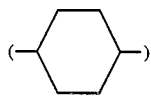

or 1.4-substituted bicyclo[2,2,2]octane ring or

2,5-substituted pyrimidine ring

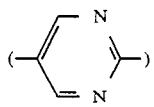

or 2,5-substituted 1,3-dioxane ring

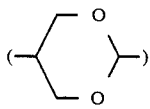

or when ring B is 1,4-substituted benzene ring, then ring A indicates 1,4-trans-substituted cyclohexane ring or 2,5-substituted pyrimidine ring or 1,4-substitutedbicyclo [2,2,2,]octane ring or 2,5-substituted 1,3-dioxane ring. R is a normal alkyl chain $C_nH_{2n+1}$, or a non-branched alkoxy group $C_nH_{2n+1}O$ or an alkylcarboxylic group $C_nH_{2n+1}COO$ or an alkylcarbonato group $C_nH_{2n+1}OCOO$ or branched alkyl $CH_3-CH_2-CH(CH_3)-(CH_2)_k$ or branched chain alkoxy group $CH_3-CH_2-CH(CH_3)-(CH_2)_k-O$, where n is an integer number and assumes values from 1 to 12, k is an integer number assuming values from 1 to 3, l is an integer number 1 or 0 and m is an integer number 1 or 0 fulfiling the condition that $l+m>0$ and if ring A denotes 1,4-substituted bicyclo[2,2,2]octane ring also $l+m=0$

DETAILED DESCRIPTION OF THE INVENTION

The compounds of general formula I, when $l=0$ and $m=0$, are transformed into a bi-ring compound of sub-formula Ia:

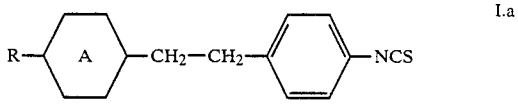
I.a or when $l=0$ and $m=1$ are transformed into a three ring compounds of sub-formula Ib:

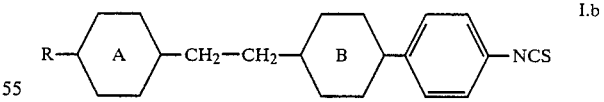
I.b or when $l=1$ and $m=0$ are transformed into a three ring compound of sub-formula Ic:

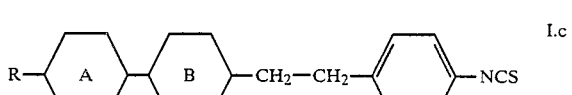
I.c

According to the definition rings A and B and indicators l and m the following compounds are assigned to the general formula I:

for l = 0 and m = 0
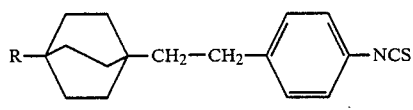
for l = 0 and m = 1
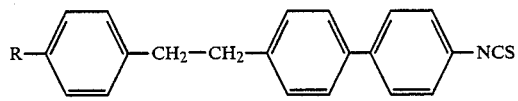
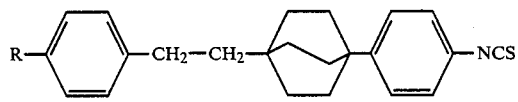
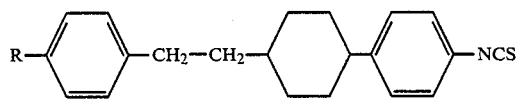
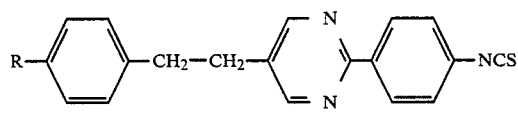
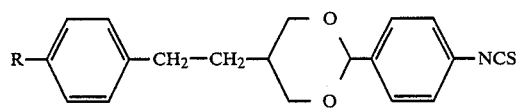
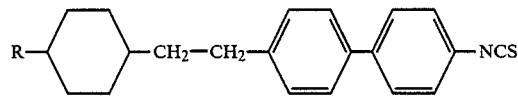
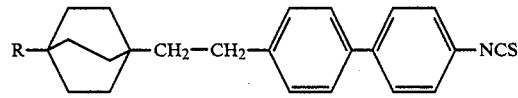
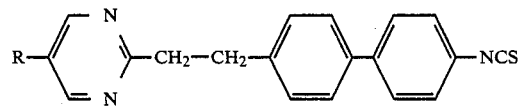
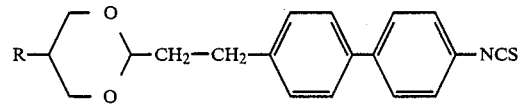
for l = 1 and m = 0
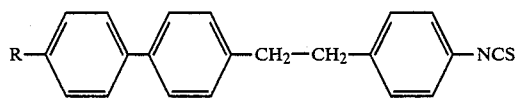
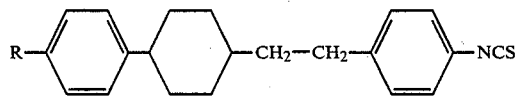
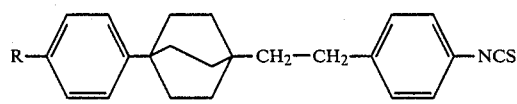

-continued
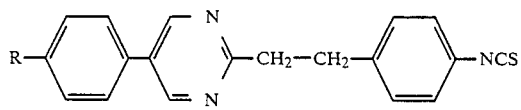
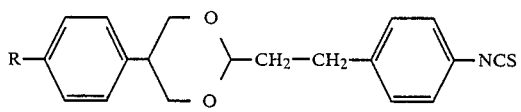
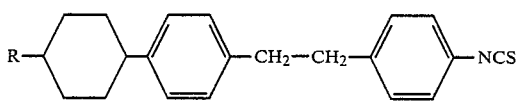
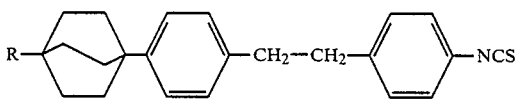
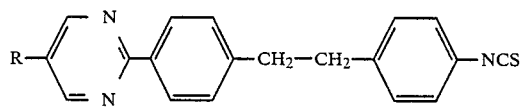
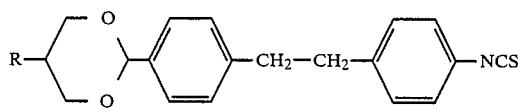
for l = 1 and m = 1
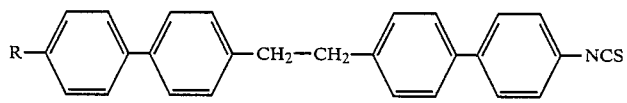
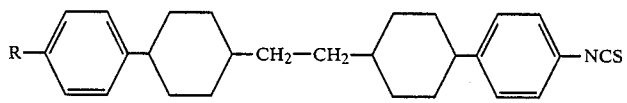
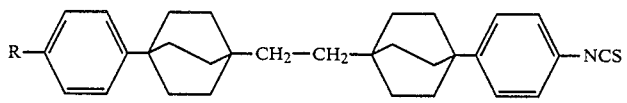
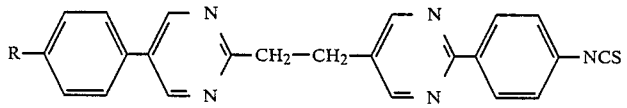
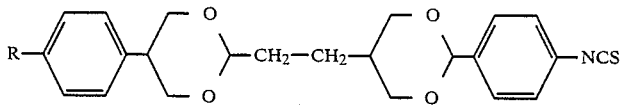
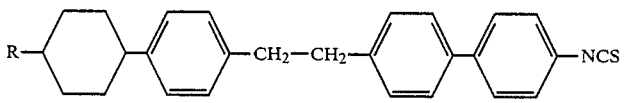
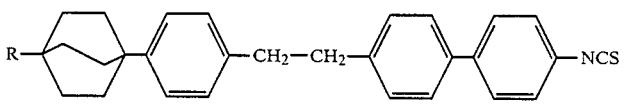

$$R-\underset{N}{\overset{N}{\langle\phantom{x}\rangle}}-\langle\phantom{x}\rangle-CH_2-CH_2-\langle\phantom{x}\rangle-\langle\phantom{x}\rangle-NCS$$

$$R-\underset{O}{\overset{O}{\langle\phantom{x}\rangle}}-\langle\phantom{x}\rangle-CH_2-CH_2-\langle\phantom{x}\rangle-\langle\phantom{x}\rangle-NCS$$

Preparation of liquid crystalline compounds of general formula I in accordance with the invention is charakteristic in that the amine of formula II:

$$R-(A)-[(B)]_l-CH_2-CH_2-[(B)]_m-\langle\phantom{x}\rangle-NH_2 \qquad II.$$

in which the notations are the same as in formula I is treated as shown on scheme 1:

(a) thiophosgene in the presence of an organic solvent preferably chloroform and a base compound preferably calcium carbonate or sodium bicarbonate:

(b) carbon disulfide in the presence of solvent and a tertiary amine; the obtained trialkyloamonium dithiocarbamate is separated from the solution, and dissolved in an organic solvent and treated with an acid chloride in the presence of a tertiary amine; benzene is preferably applied as the solvent; triethylamine—as the tertiary amine, ethyl chloroformate—as the acid chloride;

(c) carbon disulfide in the presence of an organic solvent preferably ether and dicyclohexylcarbodiimide.

The final product of all the mentioned ways of preparing liquid crystalline compounds is then separated by the known methods as evaporating or crystallization, or washing, drying etc.

Scheme 1

$$R-(A)-[(B)]_l-CH_2-CH_2-[(B)]_m-\langle\phantom{x}\rangle-NH_2 \qquad II.$$

| CSCl$_2$ | 1. CS$_2$, Et$_3$N | CS$_2$ |
| CaCO$_3$(NaHCO$_3$) | 2. ClCOOEt | H$_{11}$C$_6$N=C=N—C$_6$H$_{11}$ |

$$R-(A)-[(B)]_l-CH_2-CH_2-[(B)]_m-\langle\phantom{x}\rangle-NCS \qquad I.$$

Amines of formula II being the substrate for preparing compounds I of this invention can be obtained in numerous ways:

Method I, which is a general method of obtaining compounds of formula II, for cases when m=0, is shown in scheme 2.

Scheme 2

$$R-(A)-[(B)]_l-CH_2CH_2Y + \langle\phantom{x}\rangle-NH_2$$

$$\downarrow ZnCl_2$$

-continued
Scheme 2

$$R-(A)-[(B)]_l-CH_2CH_2-\langle\phantom{x}\rangle-NH_2$$

(II for m = 0),

In this method compound III, which is β-substituted athanol oe its halogen derivatives is heated with aniline in the presence of ZnCl$_2$, similarly as it has been described in the Polish Pat. No. 124624 for obtaining p-alkylaniline. The substrate III may be obtained from compounds IV according to the procedure given by Zytynski in Mol.Cryst. Liq.Cryst. 87,109 (1982) for p-pentyl-p'-(2-chloroethyl)-biphenyl.

Method II shown in scheme 3 concerns compounds of formula II, in which rings B are the benzene ones and m=0 or m=1 and l=1.

Scheme 3

$$R-(A)-\langle\phantom{x}\rangle + ClCOCH_2-[\langle\phantom{x}\rangle]_m-\langle\phantom{x}\rangle-NO_2$$
IV. \qquad V.

step 1 $\downarrow$ AlCl$_3$ $$R-(A)-\langle\phantom{x}\rangle-COCH_2-[\langle\phantom{x}\rangle]_m-\langle\phantom{x}\rangle-NO_2$$
VI.

step 2 $\downarrow$ H$_2$N—NH$_2$ ethylene glicol, KOH $$R-(A)-\langle\phantom{x}\rangle-CH_2-CH_2-[\langle\phantom{x}\rangle]_m-\langle\phantom{x}\rangle-NH_2$$

(II for l = 1),

The substrate IV is easily obtained according to the method described by Dabrowski in Mol.Liq.Cryst., 58, 251, (1980), when ring A is the benzene one, or by Gray's in J. C. S. Perkin II (1981), 26, when A is the bicyclooctane one.

The second substrate, compound V, may be obtained by nitration of phenyl acetic or biphenylacetic acid or benzyl cyanide by the method described in Practical Organic Chemistry, A. Vogel, WNT 1984, p. 536.

In the first step compound V reacts with the phenyl acetic or biphenyl acetic chloride giving the keto derivative VI, which in the second stage, in the conditions of the Wolff-Kishner reaction is simultaneously reduced on the nitro group and the carbonyl group. When l=0 one can start from

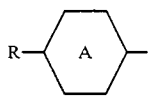

substituted acetyl chloride and benzene or biphenyl as second substrate.

The obtaining ketocompound is in similar way reduced as compound IV then acetylates and transformed to amine II via ketoxime and anilide. The remaining methods III, IV, V, VI, are especially advantageous for preparing some compounds of formula II. Method III can be applied for preparing compound II when ring A is the benzene ring and B is the pyrimidine ring and m=0.

Scheme 4

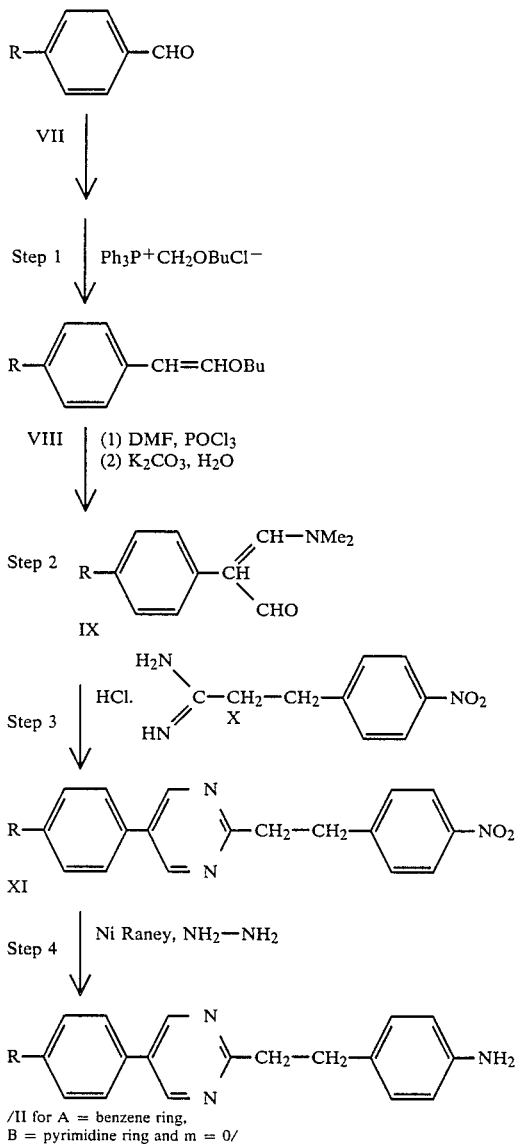

/II for A = benzene ring,
B = pyrimidine ring and m = 0/

Compound VII has been obtained by the Smith method, J. Org. Chem. 37 3972 (1972) and then used in the first step of the reaction conducted according to G. Wittig and M. Schlosser, Chem.Ber., 94 1373 (1961).

Step 2 has been conducted in a similar way to Z. Arnold, Coll.Czech.Chem.Comm., 26, 305 (1961). Condensation of N,N-dimethylacrolein IX with amidine X was conducted according to Zaschke, J. Pract.Chem., 317, 617 (1979), and the obtained compound XI was reduced with hydrazine by a standard method in the presence of Raney nickel.

Method IV is specific for obtaining compounds of formula II, where ring A indicates the benzene ring and ring B indicates the dioxane ring and m=0.

Scheme 5

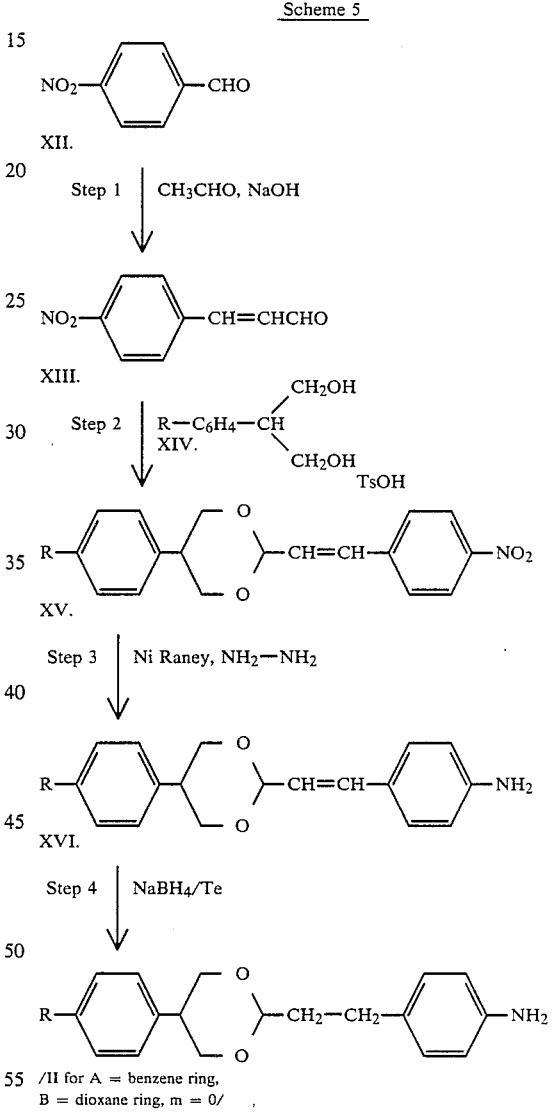

/II for A = benzene ring,
B = dioxane ring, m = 0/

The first step of this method was conducted according to T. Nishimura, Bull.Chem.Soc.Jap., 25, 54 (1952); condensation with alkylphenylpropanediol-1,3 (compound XIV) and reduction of the nitro group (steps 2 and 3) was conducted by the method described in Mol.-Cryst.Liq.Cryst., 124, 241, (1985). The reduction of the double bond was conducted according to the K. Romasamy method, Synthesis, 545 (1978).

Method V is a more general method for obtaining compounds II containing the pyrimidine ring.

Scheme 6

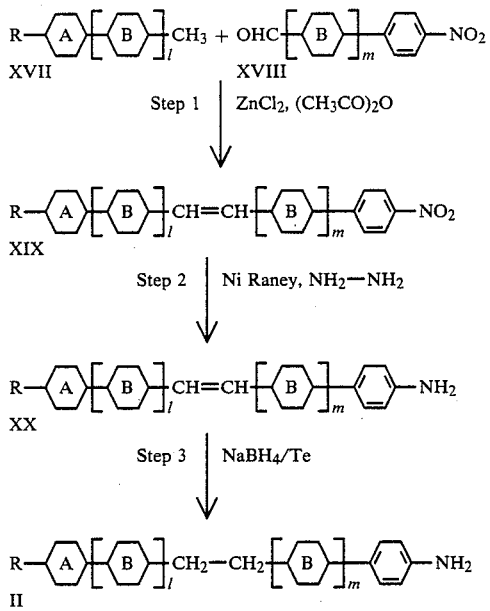

Method V shown in scheme 6, is especially advantageous for compounds II, where ring B is the pyrimidine ring and l=0, m=1 or 0.

In method V the methyl pyrimidine derivative (compound XVII) was heated in acetic anhydride in the presence of anhydrous zinc chloride and stilbene derivative was obtained (compound XIX) and reduced to the amino derivative (compound II) by and analogous method to method IV (stages 3 and 4). Method VI is a more general method of obtaining compounds II containing the dioxane ring (Scheme 7).

Raney nickel by the method described in Mol.Cryst.Liq.Cryst., 124, 241 (1985).

Compounds of the above invention, expressed by formula I will be illustrated in detalis below by examples showing the method of their preparation and also the method of preparation the essential starting compounds; especially the method of obtaining compounds of formula II will be show in detalis. Also the characteristic features of compounds thus obtained will be discussed in the examples. The used symbols indicate:

Cr—solid phase, $S_A$—smectic A phase, $S_B$—smectic B, N—nematic phase, 1 —isotropic phase. The temperatures are in all instance given in °C.

EXAMPLE 1

1-[p-(trans-4-n-heptylcyclohexyl)phenyl]-2-(p-isothiocyanato phenyl)ethane

To a mixture 50 cm³ of water, 50 cm³ of chloroform, 4 g of calcium carbonate and 3.5 g (0.03 moles) of thiophosgene, a solution 10 g (0.026 moles) of 1-[p-(trans-4-n-heptylocyclohexyl)phenyl]-2-(p-aminopenyl)ethane in 50 cm³ of chloroform was added dropwise at room temperature and the vigorous stirring. It was further stirred for two hours, and then a small quantity of 5% hydrochloric acid (20 cm³) was added dropwise and the two layers were separated. The chloroform layer was washed with water and dried over MgSO₄. After the chloroform was distilled off the solid residue was recrystallized from isopropanol using active carbon for decolouring and then twice from n-hexane and once from a mixture of methanol-chloroform. 3 g (27% yield) of 1-[p-(trans-4-n-heptylcyclohexyl)phenyl]-2-(isothiocyanatophenyl)ethane was obtained with the temperatures of phase transition Cr 71°N 118°I.

The following compounds were obtained in a similar way:

Scheme 7

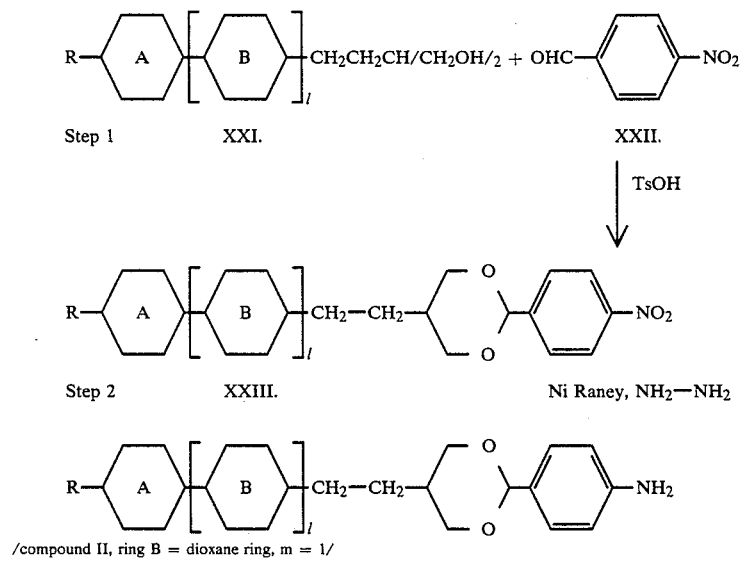

/compound II, ring B = dioxane ring, m = 1/

This method is especially prefered for obtaining compounds II, where l=0. Step 1 was conducted by heating the propandiol-1,3 derivative (compound XXI) with p-nitrobenzoic aldehyde. The nitro group is compound XXII was reduced with hydrazine in the presence of 1-[p-(trans-4-ethylcyclohexyl)phenyl]-2-(p-isothiocyanatophenyl)ethane Cr 89°I (N88°)

1-[p-(trans-4-propylcyclohexyl)phenyl]-2-(p-isothiocyanatophenyl)ethane

Cr 105°N 120°I

1-[p-(trans-4-butylcyclohexyl)phenyl]-2-(p-isothiocyanatophenyl)ethane

Cr 149°Cr$_2$61°N 113.5°I

1-[p-(trans-4-hexylcyclohexyl)phenyl]-2-(p-isothiocyanatophenyl)ethane

Cr 52°Cr$_2$60.5°N 117°I

1-[p-(trans-4-pentylcyclohexyl)phenyl]-2-(p-isothiocyanatophenyl)ethane

Cr 65°N 126°I

1-[p-(trans-4-decylcyclohexyl)phenyl]-2-(p-isothiocyanatophenyl)ethane

Cr 58°N 110°I 1-(p'-ethylbiphenyl)-2-(p-isothiocyanatophenyl)ethane

Cr 129°N 134°I 1-(p'-propylbiphenylyl)-2-(p-isothiocyanatophenyl)ethane

Cr 113°N 134°I 1-(p'-butylbiphenylyl)-2-(p-isothiocyanatophenyl)ethane

Cr 87°N 131°I 1-(p'-hexylbiphenylyl)-2-(p-isothiocyanatophenyl)ethane

Cr 56°S$_B$99.5°N 133°I 1-(p'-heptylbiphenylyl)-2-(p-isothiocyanatophenyl)ethane Cr 70°S$_B$103°N 135°I 1-(p'-decylbiphenylyl)-2-(p-isothiocyanatophenyl)ethane Cr 38°S$_B$101N°122°I 1-(p'-methylbutyl/biphenylyl)-2-(p-isothiocyanatophenyl)ethane Cr 71.5°S$_A$98°I 1-(trans-4-n-pentylcyclohexyl)-2-(p'-isothiocyanatobiphenylyl)ethane Cr 95.5°N 190°I 1-(p-n-butylphenyl)-2-[trans-4-(p-isothiocyanatophenyl)cyclohexyl]ethane Cr 58°N 110°I 1-(p-n-penytylphenyl)-2-[trans-4-(p-isothiocyanatophenylyl)cyclohexyl]ethane Cr 68.5°N 119°I 1-(p'-n-penytyloxybiphenylyl)-2-(p-isothiocyanatophenyl)ethane Cr 63°S$_B$129°N 164.5°I 1-(4-n-hexylbicyclo[2,2,2]octyl)-2-(p-isothiocyanatophenyl)ethane Cr 62°N 105°I 1-[p'-(4-n-propylbicyclo[2,2,2]octyl)phenyl]-2-(p-isothiocyanatophenyl)ethane Cr 153.5°I (N154.5°)

1-[p'-(4-n-hexylbicyclo[2,2,2]octyl)phenyl]-2-(p-isothiocyanatophenyl)ethane

Cr 106°N 156.5°I 1-(4-n-hexylbicyclo[2,2,2]octyl)-2-(p'-isothiocyanatobiphenylyl)ethane Cr 128.5°N 248°I

EXAMPLE 2

1-[5-(p-propylphenyl)pyrimidyl-2]-2-(p-isothiocyanatophenyl) ethane

To a mixture 50 cm$^3$ of water, 50 cm$^3$ of chloroform, 4 g of calcium carbonate and 3.5 g of thiophosgene, cooling to 5° a solution of 7.88 g (0.025 moles) of 1-[5-(p-propylphenyl)pyrimidyl-2]-2-(p-aminophenyl)ethane in 50 cm$^3$ of chloroform was added dropwise and then vigorous stirrin which was then continued for two hours. Next, the mixture was filtered and phases were separated. Chloroform phase was dryed over MgSO$_4$ and evaporated. The crude product was then crystallized from methanol-ether sollution (3:1) and three times from hexane-benzene sollution (95:5) 4.5 g (50.2% yield) of 1-[5-(p-propylphenyl)pyrimidyl-2]-2-(p-isothiocyanatophenyl)ethane was obtained with phase transition:

Cr 151 I

In the same way were obtained:
1-[5-(4-n-butylphenyl)pirymidyl-2]-2-(p-isothiocyanatophenyl) ethane Cr 137.5 S$_A$ 142I 1-[5-(4-n-hexylphenyl)pirymidyl-2]-2-(p-isothiocyanatophenyl) ethane Cr 127 S$_A$ 149 I.

EXAMPLE 3

1-(p-n-butylphenyl)-2-[trans-2-(p-isothiocyanatophenyl)-1,3-dioxyl-5]ethane

A mixture 11.2 g of CaCO$_3$, 50 cm$^3$ of water, 35 cm$^3$ of chloroform, 8.4 g (0.078 mole) of thiophosgene was cooled to 0° and this temperature a solution of 19 g (0.056 mole) of 1-(p-n-butylphenyl)-2-[2-(p-aminophenyl)-1,3-dioxyl-5]ethane in 100 cm⁰ of chloroform was added dropwise while stirring. The mixture was stirred for four hours, and then the layres were separated. The chloroform layer was washed with water and dried over anhydrous MgSO$_4$, filtred through silica gel. After the chloroform was evaporated the solid product was recrystallized from a methanol-tetrahydrofuran (1:4) and then from hexane. 10 g (47% yield) of 1-(p-n-butylphenyl)-2-[trans-2-(p-isothiolcyanatophenyl)-1,3-dioxyl-5]ethane was obtained. The temperatures of phase transition Cr 94°N 113°I.

The following compounds were obtained in a similar way:
1-(p-n-pentylphenyl)-2-[trans-2-(p-isothiocyanatophenyl)-1,3-dioxyl-5]ethane. Cr 92°N 118°K.
1-[5-(n-pentyl-1,3-dioxyl-2]-2-(p'-isothiocyanatobiphenylyl) ethane
1-[5-(p-n-pentylphenyl)-1,3-dioxyl-2]-2-(p'-isothiocyanatobiphenylyl)ethane

EXAMPLE 4

1-(p'-n-hexylbiphenylyl)-2-(p-isothiocyanatophenyl)ethane 18 g (0.05 moles) 1-(p'-n-hexylbiphenylyl)-2-(p-aminophenyl)ethane was dissolved in 200 cm³ of benzene and 25 cm³ of hexane. Then 14 cm³ (0.1 mole) of triethylamine and 6 cm³ (0.1 mole) carbon disulphide was added to the solution. The components were well stirred and left in the fridge for 48 hours. A yellow salt triethyloamonium ditiocarbonate was preciptitated and filtered off and then washed with ether. The obtained produce was dissolved in 100 cm³ of chloroform, 10.5 cm³ of triethylamine was added to the solution and after cooling to 0° 7 g (0.075 mole) of ethyl chloroformate was added droppwise to the continuously stirring solution. After an hour 100 cm³ of 3N hydrochloric acid was poured into the reaction mixture, the layers were separated and the chloroform one was washed twice with water and dried MgSO$_4$. After distilling chloroform off the solid residue was crystallized from isopropanol, then twice from n-hexane and once from a composition of methanol-chloroform. 5 g (25% yield) of 1-p'-n-hexylbiphenylyl)-2-(p-isothio-cyanatophenyl)ethane was obtained. The temperatures of phase transition: Cr 56°S$_B$99.5°N133°I.

EXAMPLE 5

1-(p'-n-heptylbiphenylyl)-2-(p-isothiocyanatophenyl)ethane 10.2 g (0.05 mole) of dicyclohexylcarbodiimide (DCC) was dissolved in 50 cm³ of dry ether, 60 g of carbon disulphide, and 16.7 g (0.945 mole) of 1-(p'-n-heptylbi-phenylyl-2-(p-aminophenyl)ethane in 50 cm³ of ether were added to the solution. The mixture was left for a few hours and then crystals of dicyclohexyltiourea were filtered, the filtrate was concentrated, the residue was dissolved in benzene and then filtered through a layer of silica gel. The filtrate was concentrated until dry and the solid was recrystallized from isopropanol and then twice from n-hexane 4 g (21% yield) of 1-(p-n-heptylbiphenylyl)-2-(p-isothio cyanatophenyl)ethane was obtained. The temperatures of phase transition: Cr 70°S$_B$103°N135°I.

EXAMPLE 6

1-(p'-n-hexylbiphenylyl)-2-(p-aminophenyl)ethane

Step 1

A solution containing 52.4 g (0.26 mole) of p-nitrophenylacetic acid chloride in 300 cm³ methylene chloride was added dropwise, at room temperature, to a stirred mixture composed of 40 g (0.3 mole) anhydrous aluminium chloride and 200 cm³ of methylene chloride. Then the mixture was cooled to 0° and in this temperature a solution 59.5 g (0.25 mole) p-hexylbiphenyl in 200 cm³ methylene chloride was added dropwise. The reaction mixture was stirred for 4 hours at 0° and then it was poured into water with ice. The layers were separated and the organic one was washed four times with water and dried over anhydrous MgSO$_4$ and the solvent was distilled off under vacuum and the raw product was recrystallized from acetone giving 71 g (70.8% yield) of 4-n hexyl-4'-(p-nitrophenylacetyl)biphenyl with melting point 132–133°.

The following compounds were obtained in a similar way:
4-ethyl-4'-(p-nitrophenylacetyl)biphenyl, melting point 190°.
4-n-propyl-4'-(p-nitrophenylacetyl)biphenyl, melting point 163°.
4-n-butyl-4'-(p-nitrophenylacetyl)biphenyl, melting point 155°.
4-n-pentyl-4'-(p-nitrophenylacetyl)biphenyl, melting point 133–134°.
4-n-heptyl-4'-(p-nitrophenylacetyl)biphenyl, melting point 133–134°.
4-n-decyl-4'-(p-nitrophenylacetyl)biphenyl, the temperatures of phase transition:

Cr 125°S$_A$134°I 4-n-pentyloxy-4'-(p-nitrophenylacetyl)biphenyl, temperatures of phase transition: Cr 151–152°N156.5°I.
4-(2-methylbutyl)-4'-(p-nitrophenylacetyl)biphenyl, melting point 103–104°.
4-[trans-4-(p-nitrophenyl)cyclohexylacetyl]-n-pentylbenzene melting point 100–101°.

Step 2

A mixture containing 64 g (0.16 mole) of 4-hexyl-4'-(p-nitro phenylacetyl)biphenyl, 50 g (0.8 mole) 80% hydrazine hydrate and 700 cm³ of diethylene glycol was heated to 140–145° for 6 hours. Then it was cooled to room temperature and 27 g (0.48 mole) of potassium hydroxide was added and again heated distilling off volatile components until a temperature 200° was reached. Then it was boiled under reflux condenser at 200° for 4 hours. After cooling the reaction mixture was diluted with water. The precipitated amine was extracted with toluene (1.51), the toluene solution was filtered through a layer of active carbon and dried MgSO$_4$. The solvent was distilled off and the residue recrystallized from isopropanol. 25 g of 1-(p'-hexylbiphenylyl)-2-(p-aminophenyl)ethane (43% yield) was obtained with melting point 107–110°.

EXAMPLE 7

1-(p'-n-pentylbiphenylyl)-2-(p-aminophenyl)ethane 18.6 g (0.2 mole) of distilled aniline, 57.4 g (0.2 mole) of 1-(p-n-pentylbiphenylyl)-2-chloroethane, 20.4 g of remelted ZnCl$_2$ were heated for 10 hours at 220°. Then the mixture was cooled to 80°, 200 cm³ of ethanol was added and the lot was boiling under reflux for 4 hours. White crystalline precipitate was filtered off and heated for 2 hours with 200 cm³ of 10% aqueous NaOH solution. The separated oil substance was extracted with toluene, the extract was dried over solid KOH and toluene was distilled off. The residue was recrystallized from isopropanol. 26.5 g (35% yield) of 1-(p'-n-pentyl-biphenylyl)-2-(p-aminophenyl)ethane was obtained, melting point 110–113°.

EXAMPLE 8

1-[p-(trans-4-heptylcyclohexyl)phenyl]-2-(p-aminophen

Step 1

30 g (0.15 mole) of p-nitrophenyl acetic acid chloride dissolved in 150 cm³ of methylene chloride was added dropwise to a stirred mixture of methylene chloride and 25.7 g (0.195 mole) of anhydrous aluminium chloride. Then it was cooled to 0° and at this temperature a solution containing 38.8 g (0.15 mole) of 4-heptylcyclohexylbenzene with about 70% of the trans isomer and 150 cm³ of methylene chloride was added dropwise. The reaction mixture was stirred for 4 hours 0° and then poured into water with ice. The organic layer was separated, washed with water and dried over MgSO₄. Methylene chloride was distilled off and the residue recrystallized from acetone. 23 g (36% yield) of 4-(p-nitrophenylacetyl)-1-(trans-4-heptylcyclohexyl)-benzene was obtained, melting point 145–146°.

The following compounds were obtained in a similar way:

4-(p-nitrophenylacetyl)-1-(trans-4-n-ethylcyclohexyl)-benzene, melting point 175°.
4-(p-nitrophenylacetyl)-1-(trans-4-n-propylcyclohexyl)-benzene, melting point 163°.
4-(p-nitrophenylacetyl)-1-(trans-4-n-butylcyclohexyl)-benzene, melting point 154°.
4-(p-nitrophenylacetyl)-1-(trans-4-n-pentylcyclohexyl)-benzene, melting point 144°.
4-(p-nitrophenylacetyl)-1-(trans-4-n-hexylcyclohexyl)-benzene melting point 145°.
4-(p-nitrophenylacetyl)-1-(trans-4-n-heptylcyclohexyl)-benzene melting point 146°.
4-(p-nitrophenylacetyl)-1-(trans-4-n-decylcyclohexyl)-benzene, melting point 144°.

Step 2

A mixture of 22 g (0.05 mole)4-(p-nitrophenylacetyl)-1-(trans-4-heptylcyclohexyl)benzene and 13 g (0.25 mole) of 80% hydrazine hydrate and 200 cm³ diethylene glycol was heated for 6 hours at 140–145°. Then 8 g (0.15 mole) of KOH was added and the mixture was further heated to 210°, and after it was cooled, diluted with water and extracted with toluene. The toluene extract was washed with water, filtered through a layer of active carbon, dried over MgSO₄. The solvent was distilled off and the solid residue was recrystallized from isopropanol giving 11 g (56% yield) of 1-[p-(trans-4-n-heptylcyclohexyl)phenyl]-2-(p-aminophenyl) ethane, melting point 110–115°.

The following compounds were obtained in a similar way:

1-[p-(trans-4-propylcyclohexyl)phenyl]-2-(p-aminophenyl)ethane, melting point 130–131°.
1-[p-(trans-4-hexylcyclohexyl)phenyl]-2-(p-aminophenyl)ethane, melting point 117–120°.

EXAMPLE 9

1-(p-n-butylphenyl)-2-[2-trans-(p-aminophenyl)-1,3-dioxyl-5]ethane.

Step 1

A mixture of 28.3 g (0.12 mole) of 2-[2-(p-n-butylphenyl)ethyl]propane-diol-1,3, 20 g (0.13 mole) of p-nitrobenzoic aldehyde, 0.5 g of p-toluenesulfonic acid, 200 cm³ of benzene was heated under Dean-Stark trap until water evolved. Then the mixture was washed with Na₂CO₃ solution, water and dried over anhydrous MgSO₄. Benzene was distilled off, the solid residue was crystallized twice from isopropanol. 32 g (72% yield) of 1-(p-n-butylphenyl)-2-[2-trans-(p-nitrophenyl)1,3-dioxyl-5]ethane was obtained, melting point 96–98°. The following compounds were obtained in a similar way:

1-(p-n-pentylphenyl)-2-[2-trans-(p-nitrophenyl)-1,3-dioxyl-5]ethane, melting point 84–87°.
1-(p-n-hexylphenyl)-2-[2-trans-(p-nitrophenyl-1,3-dioxyl-5]ethane.

Step 2

A mixture of 30 g of 1-(p-n-butylphenyl)-2-[2-trans-(p-nitrophenyl)-1,3-dioxyl-5]ethane, 10.5 g hydrazine hydrate, 200 cm³ of methanol was heated to 45° and Raney nickel was gradually added until temperature stopped increasing. Then it was heated at refluxing for an hour, Raney nickel was filtered off and the solution cooled. 10 g (66.7% yield) of 1-(p-n-butylphenyl)-2-[2-trans-(p-aminophenyl)1,3-dioxyl-5]ethane was obtained, melting point 99–103°.

EXAMPLE 10

1-[5-(p-n-butylphenyl)pyrimidyl-2]-2-(p-nitrophenyl)ethane

Step 1

A mixture of 4.0 g (0.017 mole) of 5-(p-n-butylphenyl)-2-methylpyrimidine. 4.0 g (0.026 mole) of p-nitrobenzoic aldehyde, 1 g of ZnCl₂, 10 cm³ of acetic anhydride was refluxed for 6 hours. Then the reaction mixture was poured onto water with ice and extracted with 250 cm³ of benzene. The extract was dred over MgSO₄ end benzene was distilled off. The residue was crystallized from a mixture of methanol-tetrahydrofurane (3:1) and twice from ethanol, 1 g (16% yield) of 1-[5-(p-n-butylphenyl)pyrimidyl-2]-2-(p-nitro phenyl)ethane was obtained, temperatures of phase transition Cr 170 $S_A$ 202 N 245 I.

Step 2 and 3

The nitro compound obtained in step 1 was reduced by hydrazine and Raney nickel in the same way as it was described in example 9. 0.78 g of 1-[5-(p-n-butylphenyl)-pyrimidyl-2]-2-(p-aminophenyl)ethane was obtained. It was then added to a suspension prepared from tellurium powder (0.05 g) and sodium borohydride (0.03 g) in ethanol (5 cm³). The mixture was heated under reflux for 4 hour and then poured into ice-water (5 cm³). The product was extracted with chloroform, the extract was dried over K₂CO₃ and chloroform was evaporated. The residue was crystallized from ethanol, 0.5 g (66% yield) of 1-[5-(p-n-butylphenyl)-pyrimidyl-2]-2-(p-aminophenyl)ethane was obtained, melting point 115–117°.

The compound of the formula I can be used as components of liquid crystal mixtures, for displays, in particular operated on the principle of the twist-nematic effect (TN), the supertwistet birefrigence (SBE), the gaest-host effect and cholesteric nematic phase change effect. Liquid crystalline compositions according to the invention is a liquid crystal mixture with positive dielectric anisotropy including at least two components among which at least one component is the compounds of formula I. The amount of compounds of formula I can change in relatively wide limits, usually in a quantity exceeding 2% by weight when they haven't chiral properties. The application of liquid crystalline multi-component mixtures containing 5–40% by weight of compounds of formula I is the most advantageous. If the compounds of formula I are optically active that they can be used as chiral dopants for creation spontaneous twist in a smaller quantity, also in the quantity from 0.01 to 2% weight. Dichroic dyes for colour displaying and other non liquid crystalline compounds for modyfying the dielectric anisotropy, the viscosity and the alignment ability may be sometimes added to the mixture according to the invention. The amount of dichroic dyes is determined by the solubility, and extinction and it is usually less than 5 wt % in the all mixture. Compounds of formula I are especially advantageous components of the liquid crystalline compositions containing known liquid crystalline compounds with the isothiocyanato group. The examples of such compounds are compounds of formulae XXIII–XXIX:

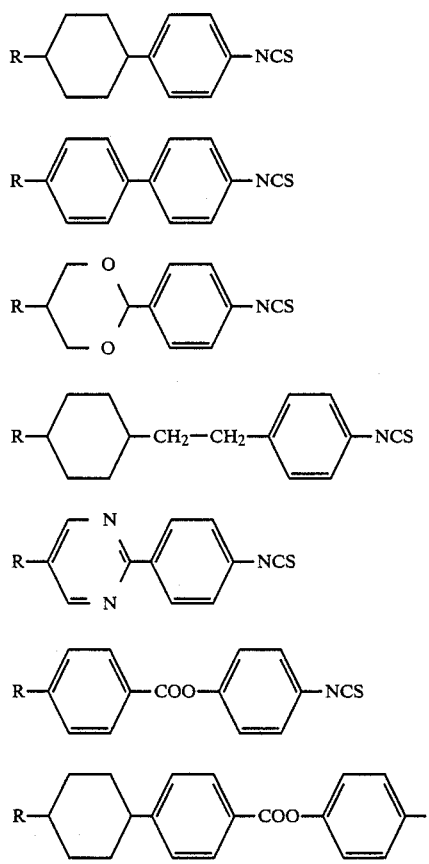

XXIII.
XXIV.
XXV.
XXVI.
XXVII.
XXVIII.
XXIX.

wherein R is a normal or branched alkyl group containing from 3 to 10 carbon atoms in the alkyl chain. They are described in Mol.Cryst.Liq.Cryst., 123, 237 (1985), 124, (241), (1985), Mol.Cryst.Liq.Cryst.Lett., 102, 155, (1985), Conference Record of the 1985 International Display Research Conference, San Diego, California, Oct. 15–17 1985. It is possible to prepare nematic mixtures and also smectic A ones with low melting points composed of the compounds of the formula XXIII to XXVIII but their clearing points are low. Therefore they can be used only as basic mixtures to which other higher claring point liquid crystalline components are added. Multicomponent mixtures manufacturing from compound of the formula XXIII and/or XXVI are favourable as the such basic mixtures because they posses strongly nematic character as it was shown in U.S. Pat. No. 4,528,116. The mixtures containing compound XXIII are useful for liquid crystal devices operated in TN or SBE mode with condition of the multiplexing control according to their steep transmission characteristics. Multicomponent mixtures composed of compound XXIII are nematics in temperature range between ($-40°$) and 45° and their typical physical properties in 20° are: the bulk viscosity n20 10 mPa s, the dielectric anisotropy $\Delta\epsilon = \epsilon_\parallel ' \epsilon_\perp \sim 8$, the optical anisotropy $\Delta n = 0.15$, the elastic constant ratio $K_{33}/k_{11}$ 1.1 and $k_{33}/k_{22}$ 2.5. Basic mixture comprising compound XXVI posses similar properties to the mentioned above one with the profiso that the elastic constants are different: elastic constant ratio $k_{33}/k_{11}$ 1.6 and $k_{33}/k_{22}$ 3.3 and they allow to obtain less steep transmission characteristics. The compound XXV, XXVII, and XXVIII can be used also to manufacturing smectic A mixtures.

The introduction of the compounds according to the present invention of the formula I to the above mentioned basic mixtures and similar ones improve their properties in desirable way and make them more adjusted to the used electrooptical effect, the construction of the display cell and the operating temperature range. The compounds of the formula I allow to change the following properties of the basic mixtures: the clearing point and the dielectric anisotropy, and the optical anisotropy and the elastic constant ratio $k_{33}/k_{11}$ or $k_{33}/k_{22}$ and or to involve the spontaneous twist with right or left helical sense. The clearing point of basic mixture is always increased, the dielectric or optical anisotropy are usually increased bat can be also decreased, but in a smaller degree. All compounds of the formula I posses the ability to increase clearing point of basic mixtures, but two and three cyclic compounds of subformulae Ia, Ib and Ic are more preferably than the four ring ones of this invention. Especially the compounds given bellow are dissolving easily in liquid crystalline basic mixtures and therefore they are recomended as components of the mixture for operating in low temperatures:

1-(4-n-butylbicyclo[2,2,2]octyl)-2-(p-isothiocyanatophenyl)-ethane
1-(4-n-pentylbicyclo[2,2,2]octyl)-2-(p-isothiocyanatophenyl) ethane
1-(4-n-hexylbicyclo[2,2,2]octyl)-2-(p-isothiocyanatophenyl) ethane
1-(4-n-heptylbicyclo[2,2,2]octyl)-2-(p-isothiocyanatophenyl) ethane
1-(4-n-octylbicyclo[2,2,2]octyl)-2-(p-isothiocyanatophenyl) ethane
1-(p-n-butylphenyl)-2-(p'-isothiocyanatobiphenylyl)ethane
1-(p-n-pentylphenyl)-2-(p'-isothiocyanatobiphenylyl)ethane
1-(p-n-hexylphenyl)-2-(p'-isothiocyanatobiphenylyl)ethane 1-(p-n-heptylphenyl)-2-(p'-isothiocyanatobiphenylyl)ethane
1-(p-n-octylphenyl)-2-(p'-isothiocyanatobiphenylyl)ethane
1-(p-n-butyloxyphenyl)-2-(p'-isothiocyanatobiphenylyl)ethane
1-(p-n-pentyloxyphenyl)-2-(p'-isothiocyanatobiphenylyl)ethane
1-(p-n-hexyloxyphenyl)-2-(p'-isothiocyanatobiphenylyl)ethane
1-(p-n-butylphenyl)-2-[4-(p-isothiocyanatophenyl)cyclohexyl]ethane
1-(p-n-pentylphenyl)-2[4-(p-isothiocyanatophenyl)cyclohexyl ethane
1-(4-n-butylbicyclo[2,2,2]octyl)-2-(p'-isothiocyanatobiphenyl)ethane
1-(4-n-pentylbicyclo[2,2,2]octyl)-2-(p'-isothiocyanatobiphenyl)ethane
1-94-n-hexylbicyclo[2,2,2]octyl)-2-(p'-isothiocyanatobiphenylyl)ethane
1-(4-n-heptylbicyclo[2,2,2]octyl)-2-(p'-isothiocyanatobiphenylyl)ethane
1-(4-n-octylbicyclo[2,2,2]octyl)-2-(p'-isothiocyanatobiphenylyl)ethane
1-(trans-4-n-propylcyclohexyl)-2-(p'-isothiocyanatobiphenylyl)ethane
1-(trans-4-n-butylclohexyl)-2-(p'-isothiocyanatobiphenylyl)ethane
1-(trans-4-n-pentylcyclohexyl)-2-(p'-isothiocyanatobiphenylyl)ethane
1-(trans-4-hexylclohexyl)-2-(p'-isothiocyanatobiphenylyl)ethane
1-(trans-4-n-octylclohexyl)-2-(p'-isothiocyanatobiphenylyl)ethane
1-(p'-n-butylbiphenylyl)-2-(p-isothiocyanatophenyl)ethane
1-(p'-n-pentylbiphenylyl)-2-(p-isothiocyanatophenyl)ethane
1-(p'-n-hexylbiphenylyl)-2-(p-isothiocyanatophenyl)ethane
1-(p'-n-octylbiphenylyl)-2-(p-isothiocyanatophenyl)ethane
1-(p'-n-pentyloxybiphenylyl)-2-(p-isothiocyanatophenyl)ethane
1-[trans-4-(p-n-propylphenyl)cyclohexyl]-2-(p-isothiocyanato phenyl)ethane
1-[trans-4-(p-n-butylphenyl)cyclohexyl]-2-(p-isothiocyanato phenyl)ethane
1-[trans-4-(p-n-hexylphenyl)cyclohexyl]-2-(p-isothiocyanato phenyl)ethane
1-[trans-4-(p-n-heptylphenyl)cyclohexyl]-2-(p-isothiocyanato phenyl)ethane
1-[trans-4-(p-n-octylphenyl)cyclohexyl]-2-(p-isothiocyanato phenyl)ethane
1-[4-(p-n-butylphenyl)bicyclo[2,2,2,]octyl]-2-(p-isothicyanatophenyl)ethane
1-[4-(p-n-pentylphenyl)bicyclo[2,2,2,]octyl]-2-(p-isothicyanatophenyl)ethane
1-[p-(trans-4-n-butylcyclohexyl)phenyl]-2-(p-isothiocyanatophenyl)ethane
1-[p-(trans-4-n-pentylcyclohexyl)phenyl]-2-(p-isothiocyanato phenyl)ethane.

From the mentioned list of compounds 1-(trans-4-n-alkylcyclohexyl)-2-(p'-isothiocyanatobiphenyl)ethane and 1-(p-n-alkylbiphenylyl)-2-(p-isothiocyanatophenyl)ethane increase the viscosity of mixture in the smallest step. The following compounds can be used for decreasing optical anisotropy of basic mixture in a small degree.

1-(4-n-hexylbicyclo[2,2,2]octyl)-2-(isothiocyanatophenyl) ethane
1-(4n-heptylbicyclo[2,2,2]octyl)-2-(isothiocyanatophenyl) ethane
1-(4n-octylbicyclo[2,2,2]octyl)-2-(p-isothiocyanatophenyl) ethane
1-(4-n-decylbicyclo[2,2,2]octyl)-2-(p-isothiocyanatophenyl) ethane.

The other compound of formula I will be increasing optical anisotropy in a very degree but the most the compounds with benzene and pirymidine rings. The following compounds are preferred to used for increasing dielectric anisotropy of basic mixture.

1-[5-n-butylpyrimidyl-2]-2-(p'-isothiocyanatobiphenylyl) ethane
1-[5-n-pentylpyrimidyl-2]-2-(p'-isothiocyanatobiphenylyl) ethane
1-[5-n-hexylpyrimidyl-2]-2-(p'-isothiocyanatobiphenylyl) ethane
1-[5-n-butyl-1,3-dioxyl-2]-2-(p'-isothiocyanatobiphenylyl) ethane
1-[5-n-hexyl-1,3-dioxyl-2]-2-(p'-isothiocyanatobiphenylyl) ethane
1-[p-(5-n-butylpyrimidyl-2)phenyl]-2-(p'-isothiocyanatobi phenylyl)ethane
1-[p-(5-n-hexylpyrimidyl-2)phenyl]-2-(p'isothiocyanatobi phenylyl)ethane
1-[5-(p-n-butylpyrimidyl-2]-2-(p'-isothiocyanatobiphenylyl) ethane
1-[5-(p-n-hexylpyrimidyl-2]-2-(p'-isothiocyanatobiphenylyl) ethane
1-[5-(p-n-butylphenyl)-1,3-dioxyl-2]-2-(p'-isothiocyanatobi phenylyl)ethane
1-[5-(p-n-hexylphenyl)-1,3-dioxyl-2]-2-(p'-isothiocyanatobi phenylyl)ethane
1-[5-(p-n-butylphenyl)pyrimidyl-2]-2-[2-(p-isothiocyanatophenylpyrimidyl-5]ethane
1-[5-(p-n-hexylphenyl)pyrimidyl-2]-2-[2-(p-isothiocyanatophenyl)pyrimidyl-5]ethane The following compounds can be used for involving spontaneous twist in the nematic or smectic mixtures.

1-[p'-(2-methylbutyl)biphenylyl]-2-(p-isothiocyanatophenyl) ethane
1-[p'-(3-methylpentyl)biphenylyl]-2-(p-isothiocyanatophenyl) ethane
1-[p'-(4-methylhexyl)biphenylyl]-2-(p-isothiocyanatophenyl) ethane
1-[p'-(2-methylbutyloxy)biphenylyl]-2-(p-isothiocyanatophenyl)ethane
1-[p'-(3-methylpentyloxy)biphenylyl]-2-(p-isothiocyanatophenyl)ethane
1-[5-(p-2-methylbutylphenyl)-1,3-dioxyl-2]-2-(p-isothiocyanatophenyl)ethane
1-[5-(p-2-methylbutylphenyl)pirymidyl]-2-(p-isothiocyanato phenyl)ethane The helical sense of these compounds is well known experts.

Compounds of formula I according to the invention can also be applied as components of liquid crystalline mixtures composed simultaneously of known liquid crystalline compounds, the molecules of which have a terminal isothiocyanato group and compounds, the molecules of which do not have a terminal isothiocyanato group, but have other terminal groups such as cyano, alkyl and alkoxy groups. The examples of such liquid crystalline compounds are the compounds of formula XXX–XLVI and they are given bellow:

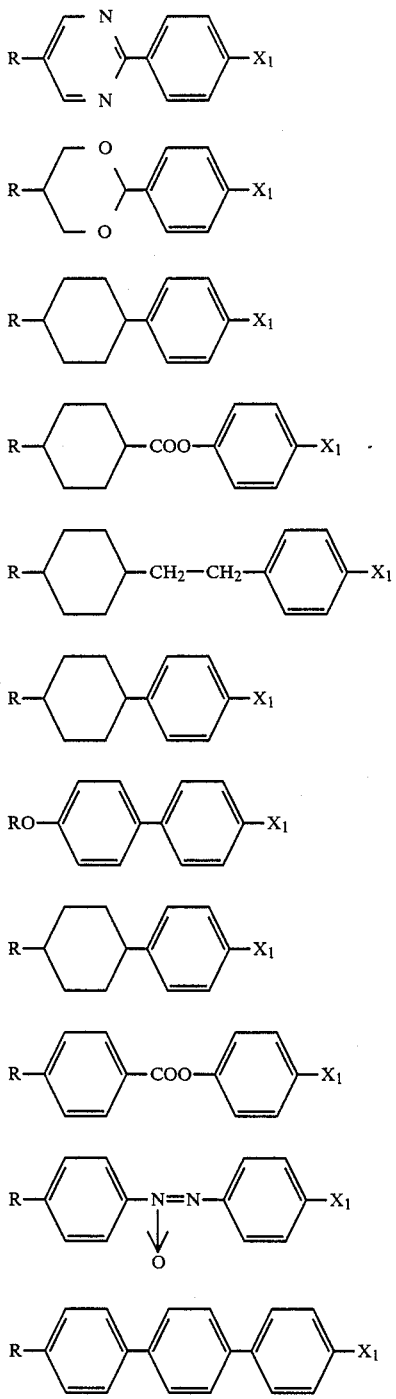

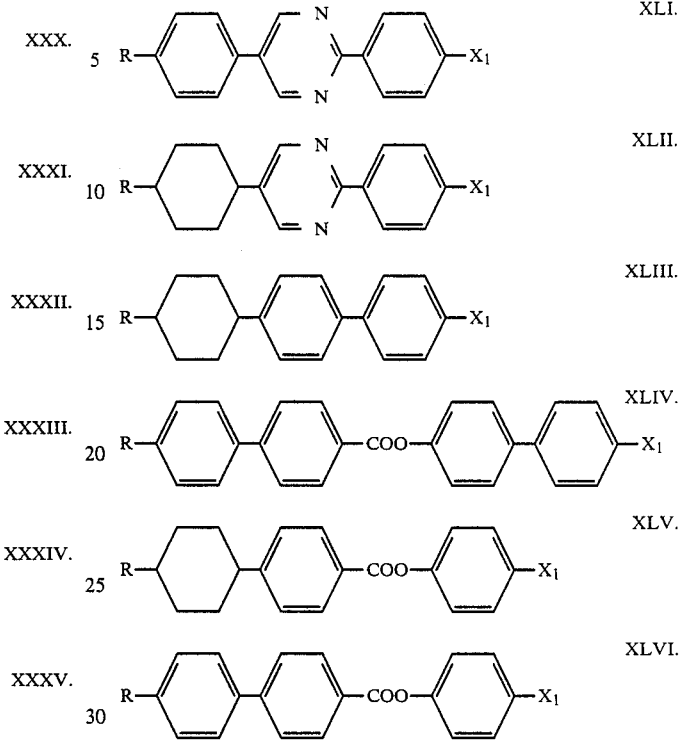

In formulae XXX–XLVI R indicates an alkyl group and $X_1$ is the cyano group or the alkoxy group. With respect to above mentioned compounds, the most advantageous ones are those characterized by a large positive dielectric anisotropy. The examples of mixtures prepared-according to the present invention and their characteristic features are shown below. The enclosed examples are given in order to illustrated the scope of this invention, however, withoute limiting the range of the invention.

EXAMPLE 11

The basic mixture is prepared consisting of:

| | |
|---|---|
| 4-(trans-4-n-propylcyclohexyl)-1-isothiocyanato-benzene | 40.00% wt. |
| 4-(trans-4-n-hexylcyclohexyl)-1-isothiocyanato-benzene | 42.00% wt. |
| 4-(trans-4-n-octylcyclohexyl)-1-isothiocyanato-benzene | 18.00% wt. |

Next the mixtures B are prepared including 90% wt. mixture A and 10% wt. compound I, their viscosity and clearing point are compared with A below:

| L.p | Mixture | viscosity $n_{20}O$ mPa s | clearing point |
|---|---|---|---|
| 1. | A | 10.9 | 41.5 |
| | Mixture B (A and . . .) | | |
| 2. | 1-(4-n-hexylbicyclo[2,2,2]-octyl)-2-(p-isothiocyanatophenyl)ethane | 11.5 | 47.5 |
| 3. | 1-[p-(trans-4-n-hexylcyclohexyl)phenyl]-2-(p-isothiocyanatophenyl)ethane | 12.7 | 48.5 |

-continued

| L.p | Mixture | viscosity $n_{20}O$ mPa s | clearing point |
|---|---|---|---|
| 4. | 1-[p-(trans-4-n-heptylcyclohexyl)phenyl]-2-(p-isothiocyanatophenyl)ethane | 11.6 | 50 |
| 5. | 1-[p-n-hexylbicyclo[2,2,2]-octyl)phenyl]-2-(p-isothiocyanato pheny)ethane | 12.2 | 51 |
| 6. | 1-(p'-n-hexylbiphenylyl-2-(p-isothiocyanatophenyl)ethane | 11.7 | 50 |
| 7. | 1-(p'-n-heptylbiphenyly-2-(p-isothiocyanatopheny)ethane | 12.2 | 49 |
| 8. | 1-(trans-4-pentylcyclohexyl)-2-(p-isothiocyanatobiphenyl)ethane | 10.8 | 60 |
| 9. | 1-[4-n-hexylbicyclo[2,2,2]-ocytl]-2-(p-isothiocyanatobiphenylyl)ethane | 11.5 | 66 |

EXAMPLE 12

A composition in % by weight.

| | |
|---|---|
| 4-(trans-4-n-propylcyclohexyl)-1-isothiocyanatobenzene | 26 |
| 4-(trans-4-n-hexylcyclohexyl)-1-isothiocyanatobenzene | 27.3 |
| 4-(trans-4-n-octylcyclohexyl)-1-isothiocyanatobenzene | 11.7 |
| 4-pentyl-4'-isothiocyanatobiphenyl | 15 |
| 1-(p'-n-heptylbiphenylyl)-2-(p-isothiocyanatophenyl)ethane | 10 |
| 1-[p-(trans-4-n-heptylcyclohexyl)phenyl]-2-(p-isothiocyanato phenyl)ethane | 10 | is a nematic in the temperature range from (−35°) to 59°.

At 20° it is characterized by the following parameters: viscosity, $\eta = 12$ mPa s, dielectric anisotropy, $\Delta\epsilon = \epsilon_{||} - \epsilon_{\perp} = +g$ optical anisotropy, $\Delta n = n_e - n_o = 0.22$.

The liquid crystalline cell of thickness 10 μm filled by this composition has the following electrooptical parameters

| | Temperature | | | |
|---|---|---|---|---|
| | −20° | 0° | 20° | 40° |
| Threshold voltage, $V_{10\%}$(Volt) | 2.0 | 1.8 | 1.2 | 1.5 |
| Saturation voltage $V_{90\%}$(Volt) | 3.0 | 2.8 | 2.7 | 2.4 |
| Rise time, $T_{on}10-90\%$ (ms) | 300 | 100 | 95 | 90 |
| Decay time $T_{off}90-10\%$ (ms) | 300 | 170 | 160 | 160 |

EXAMPLE 13

0.4% by weight of a blue dichroic dye of formula (given below) was added to the composition of content given in example 12

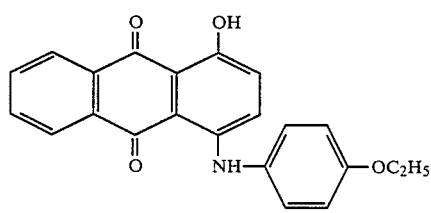

A high display contrast, dichroic ratio CR=10, and order parameter S=0.75 were observed for this composition.

EXAMPLE 14

A composition of the following content was prepared:

| | |
|---|---|
| Composition from example 12 | 97% by weight |
| Optically active 5-(2-methylbutyl)-2-(p-isothiocyanatophenyl)-1,3-dioxane | 3% by weight |

This composition shows the cholesteric-nematic phase transition for voltage 4V, at 20°, and the reverse nematic-cholesteric transition is observed for voltage IV.

EXAMPLE 15

A composition in % by weight.

| | |
|---|---|
| 4-(trans-4-n-propylcyclohexyl)-1-isothiocyanatobenzene | 25.9 |
| 4-(trans-4-n-hexylcyclohexyl)-1-isothiocyanatobenzene | 27.2 |
| 4-(trans-4-n-octylcyclohexyl)-1-isothiocyanatobenzene | 11.6 |
| 5-n-pentyl-2-(p-cyanophenyl)pyrimidine | 5.0 |
| 1-[p-(trans-4-n-heptylcyclohexyl)phenyl]-2-(p-isothio cyanatophenyl)ethane | 9.9 |
| 1-(p'-n-hexylbiphenylyl)-2-(p-isothiocyanatophenyl)ethane | 10.0 |
| 5-(p-n-butylphenyl)-2-(p-cyanophenyl)pyrimidine | 5.0 |
| 5-(trans-4-n-pentylcyclohexyl)-2-(p-cyanophenyl)pyrimidine | 5.0 |
| optically active p-(2-methylbutyl)-p'-cyanobiphenyl | 0.4 | is a nematic in the range from (−15°) to 76°. At 20° it is characterized by the following parameters: viscosity, $\eta = 17$ mPa's, dielectric anisotropy $\Delta\epsilon = +9.6$, optical anisotropy $\Delta n = 0.22$. A liquid crystalline cell of thickness 10 μm filled by this composition has a threshold voltage $V_{10\%} = 1.7$, saturation voltage $V_{90\%} = 2.4$, rise time $T_{on}10-90\% = 60$ms decay time $T_{off}90-10\% = 150$ ms.

EXAMPLE 16

A composition in % by weight.

| | |
|---|---|
| 4-(trans-4-n-propylcyclohexyl)-1-cyanobenzene | 32.28 |
| 4-(trans-4-n-pentylcyclohexyl)-1-cyanobenzene | 27.70 |
| 4-(trans-4-n-heptylcyclohexyl)-1-cyanobenzene | 20.02 |
| 1-(p'-n-hexylbiphenylyl)-2-(p-isothiocyanatophenyl)-ethane | 20.00 | is a nematic in the temperature range from (−15°) to 66°.

At 20° it is characterized by the following parameters: viscosity $\eta=22$ mPa's, $\Delta\epsilon=+9.5$ $\Delta\eta=0.15$. A liquid crystalline cell filled by this composition shows $V_{10\%}=1.6$; $V_{90\%}=2.8$; $T_{on}10-90\%=40$ ms; $T_{off}90-10\%=100$ ms.

EXAMPLE 17

A composition in % by weight:

| A composition in % by weight: | |
|---|---|
| 4-(trans-4-n-propylcyclohexyl)-1-isothiocyanatobenzene | 20 |
| 4-(trans-4-n-hexylcyclohexyl)-1-isothiocyanatobenzene | 20 |
| 1-(trans-4-n-pentylcyclohexyl)-2-(p-isothiocyanatophenyl)ethane | 15 |
| 4-n-propyl-4'-isothiocyanatobiphenyl | 10 |
| 1-(p'-n-pentylphenyl)-2-[trans-4-(p-isothiocyanatobiphenyl)cyclohexyl]ethane | 10 |
| 1-(trans-4-n-pentylcyclohexyl)-2-(p-isothiocyanaobiphenyl)ethane | 7.5 |
| 1-[p-(trans-4-n-hexylcyclohexyl)phenyl]-2-(p'-isothiocyanatobiphenylyl)ethane | 10 |
| 1-(p'-n-pentylbiphenylyl)-2-(p-isothiocyanatophenyl)ethane | 7 |
| optically active p'-(2-methylbutyloxy)phenyl p-octyloxybenzoate | 0.5 | is nematic in the temperature range from ($-30°$) to 77°.

At 25° it is characterized by the following parameters: viscosity, $\eta=13.7$ mPa's, dielectric anisotropy, $\Delta\epsilon=\epsilon||-\epsilon\bot=8.6$.

EXAMPLE 18

A composition in % by weight:

| | |
|---|---|
| 4-(trans-4-n-propylcyclohexyl)-1-isothiocyanatobenzene | 32.0 |
| 4-(trans-4-n-hexylcyclohexyl)-1-isothiocyanatobenzene | 33.6 |
| 4-(trans-4-n-octylcyclohexyl)-1-isothiocyanatobenzene | 14.4 |
| 1-(4-n-hexylbicyclo[2,2,2]octyl)-2-(p-isothiocyanatophenyl)ethane | 10.0 |
| 1-(4-n-hexylbicyclo[2,2,2]octyl)-2-(p'-isothiocyanatobiphenylyl)ethane | 10.0 | is a nematic in the temperature range from ($-31°$) to 70.5° and at 20° it has viscosity $\eta=12.5$ mPa's.

We claim:

1. Liquid crystalline ethane derivatives expressed by the general formula I:

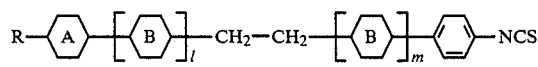

wherein
rings A and B are different or identical and when ring A denotes 1,4-substituted benzene ring then ring B denotes 1,4-substituted benzene ring or 1,4-trans-substituted cyclohexane ring or 1,4-substituted bicyclo[2,2,2]octane ring or 2,5-substituted pyrimidine ring or 2,5-substituted 1,3-dioxane ring, or when ring B denotes 1,4-substituted benzene ring then ring A denotes 1,4-trans-substituted cyclohexane ring on 1,4-substituted bicylo[2,2,2]octane ring or 2,5-substituted pyrimidine ring or 2,5-substituted 1,3-dioxane ring, and R denotes a normal alkyl chain $C_nH_{2n+1}$ or a non-branched alkoxy group $C_nH_{2n+1}O$ or an alkylcarboxylic group $C_nH_{2n+1}COO$ or an alkylcarbonato group $C_nH_{2n+1}OCOO$ or a branched alkyl chain $CH_3-CH_2-CH(CH_3)-(CH_2)_k-$ or a branched alkoxy group $CH_3-CH_2-CH(CH_3)-(CH_2)_k-O$, where n is an integer number and assumes values from 1 to 12, k is an integer number and assumes values from 1 to 3, and l is an integer number 1 or 0 and m is an integer number 1 or 0 fulfilling the condition that $l+m>0$, and if ring A denotes 1,4-disubstituted bicyclo[2,2,2]octane ring also $l+m=0$; and if ring A is 1,4-trans-substituted cyclohexane, ring B is a 1,4-substituted benzene ring, and m is 1, then l is 1.

2. Liquid crystalline ethane derivatives as claimed in claim 1 wherein $l=0$ and $m=0$ and said formula is Ia:

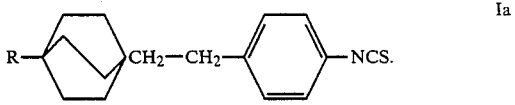

3. Liquid crystalline ethane derivatives as claimed in claim 1 wherein $l=0$ and $m=1$ and said formula is Ib:

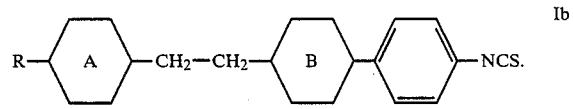

4. Liquid crystalline ethane derivatives as claimed in claim 1 wherein $l=1$ and $m=0$ and said formula is Ic:

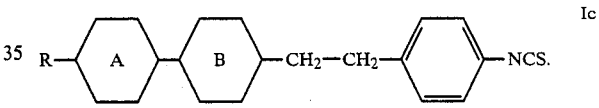

5. Liquid crystalline compositions being a mixture of at least two components specific in that at least one component belongs to the group of compounds in claim 1.

6. Compositions as claimed in claim 5 specific in that they include optically active compounds and/or dyes.

7. Compositions as claimed in claim 5 specific in that they include at least one liquid crystalline compound of formula I in a quantity of 5-40% by weight.

8. Compositions as claimed in claim 5 including at least one other liquid crystalline compound with the isothiocyanato group from 3 to 10 carbon atoms in the alkyl chain.

9. Compositions claimed as in claim 8 specific in that the other liquid crystalline compounds are 4-(trans-4-n-alkylcyclohexyl)-1-isothiocyanatobenzenes 10. Compositions claimed as in claim 8 specific in that the other liquid crystalline compounds are 4-(trans-4-n-alkylcyclohexyl)-1-isothiocyanatobenzenes and/or 4-alkyl-4'-isothiocyanatobiphenyls, and/or 5-n-alkyl-2-(isothiocyanatophenyl)pyrimidines and/or 1-(trans-4-n-alkylcyclohexyl)-2-(isothiocyanatophenyl)ethane.

11. Compositions claimed as in claim 5 including at least one other liquid crystalline compound.

12. In the liquid crystalline cell containing a liquid crystalline mixture the improvement specific in that the mixture includes a compound from claim 1.

* * * * *